United States Patent [19]

Mausner

[11] 4,032,464

[45] June 28, 1977

[54] CREAMY NAIL LACQUER REMOVER

[75] Inventor: Jack J. Mausner, East Hills, N.Y.

[73] Assignee: Helena Rubinstein, Inc., New York, N.Y.

[22] Filed: Jan. 14, 1976

[21] Appl. No.: 649,195

[52] U.S. Cl. .......................... 252/89 R; 252/170; 252/194; 252/364; 424/59; 424/61
[51] Int. Cl.$^2$ ..................... C11D 1/32; C11D 3/43; C11D 3/48
[58] Field of Search ........... 252/89, 364, 194, 170; 424/59, 61

[56] References Cited

UNITED STATES PATENTS

| | | | |
|---|---|---|---|
| 3,415,875 | 12/1968 | Luetni et al. | 424/59 X |
| 3,729,569 | 4/1973 | Charle et al. | 252/364 X |

*Primary Examiner*—Mayer Weinblatt
*Attorney, Agent, or Firm*—Burgess, Ryan and Wayne

[57] ABSTRACT

A composition useful for removing nail lacquer is disclosed. This composition comprises an aqueous solution of a chelating agent, a humectant such as an alkylene glycol, a 2-hydroxy-4-methoxy-benzophenone-5-sulfonic acid, a proteinaceous material and vitamin A and D palmitates, the aforesaid ingredients being dispersed in a thickened acetone vehicle to form a homogeneous creamy stable mixture.

5 Claims, No Drawings

CREAMY NAIL LACQUER REMOVER

The present invention relates to a novel composition. More particularly, the present invention relates to a novel composition useful for removing nail lacquer.

Many compositions are known which are useful in removing lacquer from fingernails or toenails. These compositions depend primarily upon the solvent action of acetone or acetone-like solvent to soften or dissolve the nail lacquer. After the lacquer has been dissolved or softened, it is usually removed by a gentle abrasive or by a gentle rubbing action.

Acetone or acetone-like solvents are not only quite volatile but are usually transparent. Consequently, when a consumer applies such a composition to her fingernails, excess acetone may accidentally come into contact with the surrounding skin and since body fat is readily dissolved in acetone, it is quite common that the skin may be irritated and even at times, infection may arise.

Furthermore, because of the volatility of acetone, repeated applications of this material may be necessary to remove stubborn nail lacquer. This further increases the danger of exposing the skin to further irritation and possible infection.

In addition, commercially available nail lacquers contain pigments or mixtures of pigments some of which are not readily soluble in acetone. Consequently, the removal of such nail lacquers by using an acetone-based remover may not be entirely satisfactory.

The aforesaid objectionable features of currently available nail lacquer compositions are obviated by the present composition which is in a creamy viscous form and because of these properties, the composition can be applied to a specific area with little difficulty thereby minimizing and substantially removing the danger of irritation and the possibility of infection. The present unique composition can be easily and readily applied. Further, the instant novel composition is distinguished by the fact that it is opaque and pearl-like in appearance thereby facilitating application of the composition.

According to the present invention, there is provided a novel nail lacquer remover in which the danger of the lacquer remover penetrating into surrounding skin areas is substantially eliminated. In addition, because of the coaction of the added ingredients, the novel nail lacquer remmover of the present invention has been found to be effective in removing heavily pigmented nail lacquers. Still further, the present composition is also characterized by the fact that it is extremely stable, i.e., there is minimal phase separation even after prolonged storage, at room temperature or at slightly elevated temperatures.

Broadly speaking, the present nail lacquer remover composition comprises an aqueous solution of a suitable chelating agent, a suitable humectant such as an alkylene glycol and suitably, propylene glycol, a 2-hydroxy-4-methoxy-benzophenone-5-sulfonic acid, a proteinaceous material and palmitates of vitamins A and D and a carboxy vinyl polymer. The aforesaid aqueous composition is dispersed in an acetone vehicle thickened with suitable thickening agents.

Examples of suitable chelating agents which are utilized in the present invention include disodium salt of ethylene diamine tetraacetic acid, calcium disodium acetate, and the like.

Among the suitable humectants, there are included alkylene glycols such as propylene glycol, glycerine, and the like.

In the typical practice of the present invention, at least about 0.01% by weight of the selected chelating agent, about 1.0% by weight of the selected humectant, about 0.10% by weight of 2-hydroxy-4-methoxy-benzophenone-5-sulfonic acid, about 0.05% by weight of a commercially available proteinaceous material such as protein WSP A-200 a collagen-derived protein-fatty acid condensation product (available from Goldschmidt Chemical) and about 0.05% by weight of the palmitates of vitamins A and D, are dissolved in about 5–10.0% by weight of water. To this aqueous composition, there is added about 0.5% by weight of a carboxy vinyl polymer such as those commercially available under the trademark "Carbopol 941" (available from the B. F. Goodrich Company). Typically, Carbopol 941 is most suitable for use in the present invention.

To this aqueous composition, there is added about 70.0–90.0%, by weight, of acetone, accompanied by agitation, until a homogeneous mixture is obtained. Thereafter, about 0.1–2.0%, by weight, of a suitable thickening agent is added. Examples of suitable thickening agents are methyl cellulose, ethyl cellulose, gum arabic, and a hydroxypropyl cellulose. The choice of the thickening agent is not critical but a hydroxypropyl cellulose available under the tradename "Klucel H" has been found to be most suitable because it disperses readily in the solvent system of the present invention.

The present nail lacquer remover composition exhibits a creamy texture. To improve the texture of the resulting product to a gel-like consistency, a suitable amount of triamylamine is added. Although other weak organic bases such as triethylamine have been used, the desired creamy texture of the present composition is most effectively obtained by the use of the aforesaid triamylamine. Typically, about 0.2–1.00%, by weight, of triamylamine is added to the nail lacquer remover composition.

To enhance the aesthetic effects of the present composition, suitable additives are included and these additives illustratively are, for example, dies, fragrances, and the like.

The present composition is prepared by blending the aforesaid ingredients in a suitable reaction vessel. The composition is suitably prepared at room temperature, e.g., between about 20° and 30° C.

In a commercial embodiment of the present invention, the present composition is dispersed in small vials or bottles having a volume of 10–25cc or larger. Usually, the composition is conveniently applied with a suitable applicator.

In order to further illustrate the practice of this invention the following example is included.

EXAMPLE

Into a stainless steel vessel equipped with a mixer there is added about 5 mls. of water, 0.01 grams of the disodium salt of ethylene diamine tetraacetic acid, 1 gram of propylene glycol, 0.01 gram of 2-hydroxy-4-methoxy-benzophenone-5-sulfonic acid, 0.05 grams of protein, and 0.05 grams of the palmitate of vitamins A and D. The mixture is stirred until a clear solution is formed.

In a separate vessel, 0.3 grams of D and C Red 19 in the form of an 0.1% aqueous solution is dissolved in 7 mls. of denatured alcohol. The resulting solution is added to the aforesaid aqueous solution, with mixing.

Under agitation, 0.45 grams of Carbopol 941 is gradually added to the aqueous-alcoholic solution.

When all the Carbopol has gone into solution, 70-90 grams of acetone are added to this mixture, with stirring. When a homogeneous solution has been obtained, 0.1-2.0 grams of Klucel H is added, slowly, with stirring to insure a homogeneous dispersion. There is then added 0.40% by weight, of Natural pearl (2X1PA-Rona-22% guanine in isopropyl alcohol) and perfume in an amount of about 2.5%.

To enhance the viscosity of the product and at the same time provide a neutralizing effect, 0.50 grams of triamylamine is added.

The amine of the aforesaid amine to be added is dependent upon the desired consistency of the resulting product and the amount of said amine varies between about 0.2 and 1.0 grams.

I claim:

1. A creamy composition for removing nail lacquer consisting essentially of at least about 0.01% by weight of a chelating agent selected from the group consisting of the disodium salt of ethylene diamine tetraacetic acid and calcium sodium diacetate, about 1.0% by weight of propylene glycol or glycerine humectant, 0.1% by weight of 2-hydroxy-4-methoxy-benzophenone-5-sulfonic acid, 0.05% by weight of a collagen-derived protein-fatty acid condensation product, about 0.05% by weight of the palmitate of vitamins A and D, and about 0.5% by weight of a carboxy vinyl polymer dispersed in about 70-90% by weight of acetone thickened with a thickening agent selected from the group consisting of methyl cellulose, ethyl cellulose, gum arabic and a hydroxypropyl cellulose and neutralized with about 0.2-1.0% by weight of triamylamine.

2. The composition according to claim 1 in which said chelating agent is the disodium salt of ethylene diamine tetraacetic acid.

3. A composition according to claim 1 in which said humectant is propylene glycol.

4. A composition according to claim 1 in which said thickening agent is hydroxypropyl cellulose.

5. A comosition according to claim 1 in which about 0.05% by weight of triamylamine is used.

* * * * *